US006882147B2

(12) United States Patent
Taicher et al.

(10) Patent No.: US 6,882,147 B2
(45) Date of Patent: Apr. 19, 2005

(54) NMR DETECTION OF SMALL AMOUNT OF FAST TRANSVERSAL RELAXATION COMPONENT IN MIXTURES

(75) Inventors: Gersh Zvi Taicher, Houston, TX (US); Arcady Reiderman, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 10/649,423

(22) Filed: Aug. 27, 2003

(65) Prior Publication Data

US 2004/0257076 A1 Dec. 23, 2004

Related U.S. Application Data

(60) Provisional application No. 60/406,998, filed on Aug. 29, 2002.

(51) Int. Cl.[7] .................................................. G01V 3/00
(52) U.S. Cl. ........................................ 324/303; 324/300
(58) Field of Search ............................... 324/303, 300, 324/306, 307, 309

(56) References Cited

U.S. PATENT DOCUMENTS

| 5,519,319 | A |   | 5/1996 | Smith et al. ............... 324/306 |
| 5,655,531 | A |   | 8/1997 | Nishimura et al. ....... 128/653.2 |
| 6,091,242 | A |   | 7/2000 | Hanawa ...................... 324/307 |
| 6,097,184 | A | * | 8/2000 | Flaum ......................... 324/303 |
| 6,232,778 | B1 |   | 5/2001 | Speier et al. ............... 324/303 |
| 6,331,775 | B1 | * | 12/2001 | Thern et al. ................ 324/303 |

* cited by examiner

Primary Examiner—Brij B. Shrivastav
(74) Attorney, Agent, or Firm—Madan, Mossman & Sriram, P.C.

(57) ABSTRACT

The present invention provides an improved NMR sequence for detecting small amount of a substance having short NMR transversal relaxation in the presence of a large amount of a substance having long NMR relaxation. A sequence of pulses enables the original z-oriented magnetization vector of a substance to experience differing reorientation effects based on the relative transverse relaxation rate of the substance. After said pulse sequence, a substance with long transverse relaxation experiences a substantial inversion of its nuclear magnetization vector, while a substance with short transverse relaxation experiences a nearly zero value of its vector. After a determinable wait time, said vectors can be shown to experience recognizably different behavior under the application of a CPMG sequence of pulses. Appropriate wait time can be determined by zeroing out spin echoes during the CPMG pulse sequence.

22 Claims, 6 Drawing Sheets

_US 6,882,147 B2_

NMR DETECTION OF SMALL AMOUNT OF FAST TRANSVERSAL RELAXATION COMPONENT IN MIXTURES

CROSS-REFERENCES TO RELATED-APPLICATION

This application claims priority from U.S. Provisional Patent Application Ser. No. 60/406,998 filed on 29 Aug. 2002.

BACKGROUND OF THE INVENTION

1. Field of the Invention

The invention is in the field of nuclear magnetic resonance detection. More specifically, the invention is a method for distinguishing resonance signals within a mixture of substances with different transversal relaxation rates.

2. Background of the Art

NMR relaxation measurements typically employ a static magnetic field to magnetize nuclei into an equilibrium state and an RF magnetic field orthogonal to the static magnetic field to disturb this equilibrium state of nuclear magnetization. The RF magnetic field is typically applied in a form of short pulses that give rise to free induction decay signals (FD) in a nearby NMR antenna. There a two types of relaxation processes related to energy flow and loss of coherence of spin magnetization in a population of nuclei. These relaxation processes are characterized by two relaxation times: $T_1$, the spin-lattice relaxation time, and $T_2$, the spin-spin relaxation time. The spin-lattice relaxation time is the time constant associated with the return of the longitudinal component to its thermal equilibrium state, which is parallel to the static magnetic field. The spin-spin relaxation time is the time constant associated with the decay of the transversal component of nuclear magnetization to zero. If the static magnetic field is in Z-direction of Cartesian coordinates, then the transversal component, inducing signal in the NMR antenna is in the X-Y plane. The net nuclear magnetization in the X-Y plane decays to zero due to reversible and irreversible processes of de-phasing of spin isochromats. The reversible process is a result of macroscopic inhomogeneity of the static magnetic field. This process can be refocused into a spin echo signal by employing a refocusing RF pulse.

A standard sequence of RF pulses used to measure the true transversal relaxation (not related to the macroscopic inhomogeneity of the static magnetic field) is the CPMG sequence. The CPMG sequence is described, for instance, in Experimental Pulse NMR: A Nuts and Bolts Approach by Fukushima and Roeder. This sequence comprises a first excitation RF pulse that tilts the magnetization into X-Y plane followed by a plurality of refocusing RF pulses with the carrier frequency phase shifted by 90 with respect to the excitation pulse. The period of repetition of the plurality of the refocusing pulses is twice the length of time between the center of the excitation pulse and the center of the first refocusing pulse. The spin echo signal, which results from refocusing the spin isochromats, appears between refocusing pulses. The amplitudes of the echoes represent points on a $T_2$ relaxation curve. This curve is then decomposable into exponential terms in order to differentiate between the types of substances present and/or, in the case of a fluid trapped in a porous structure, to characterize the porous media. In a mixture of substances, though, it is almost impossible to differentiate between substances just by the exponential decomposition if the substance with the shorter decay rate is of very small quantity compared to the others. A systematic error in the relaxation curve measurement caused by non-ideality of the CPMG pulse sequence and inhomogeneity of the static magnetic field will most likely exceed the signal from the short relaxation substance.

Another standard NMR technique for measuring parameters of different substances is based on analyzing the FID. In the case of a high ho nogeneity of the static magnetic field (typically a large and expensive magnet is required and a short dead time of the NMR system, a high precision of separation between substances with short and long transversal relaxation can be achieved. An appropriate analysis of the FID to improve accuracy of the separation is described, for example, in U.S. Pat. No. 5,519,319 issued to Smith et al. In many practical situations, the FID signal is defined by the inhomogeneity of the static magnetic field. No differentiation between substances is possible based on FID in this case.

Another known method for measurement of a substance with short relaxation in a mixture is described in U.S. Pat. No. 6,232,778 issued to Speier et al. The method is based on repeating the NMR experiment quickly enough in order to prevent the magnetization vector of a long NMR relaxation substance to recover its longitudinal component and therefore effectively preventing participation in the accumulated signal. Following this procedure, a multi-exponential data analysis is performed in order to filter out the residuals of the long relaxation component.

Another way to increase the precision of NMR based-differentiation between two substances in a mixture is described in U.S. Pat. No. 6,091,242 issued to Hanawa. A first RF pulse is applied to the sample in order to invert the equilibrium magnetization. For both substances, the longitudinal component of the nuclear magnetization starts to evolve toward the equilibrium. Due to difference in the longitudinal relaxation times, it is possible to choose an appropriate wait time after the application of the inversion pulse to get a zero crossing on the longitudinal magnetization curve for one of the substances in the mixture. An excitation pulse applied at the moment of the zero crossing of one substance will not cause any signal for that substance. As a result, even small amount of the other substance can be effectively detected. This method requires prior knowledge of $T_1$ or $T_l$, distribution for at least one of the substances.

The methods of Speier '778 and Hanawa '242 are ineffective if the substances with different transversal relaxation times have comparable longitudinal relaxation times. This situation occurs in many practical cases. One example is relayed to detection of a small amount of a heavy oil, for example. Herro Negro, having NMR relaxation parameters $T_2=0.5$ ms and $T_1=40$ ms, in the presence of lighter oils or water in a porous media. The substances with longer relaxation rates may have the relaxation times $T_1=T_2$ in the range 20–100 ms that are comparable with the $T_1$ of the heavy oil. Another example is found in detecting bone bound water in the human body. The bound water $T_2$ relaxation time in the frequency range 2–10 MHz is typically 0.3–0.7 ms while longitudinal relaxation time $T_1$ is 20–30 ms. The other fluids in the body have $T_2$ and $T_1$ NMR relaxation times in the range 10–200 ms.

Neither shortening the time between repetitions nor selective $T_1$ relaxation can be effective in these cases. Both known techniques will cause the same extent of NMR signal reduction for long $T_2$ relaxation components as for the short $T_2$ relaxation component.

There is a need for a new pulse sequence that enables elimination of the signal from a long relaxation substance without spoiling the relaxation signal from a short relaxation substance, even if the two substances have the same longitudinal relaxation times. The invention disclosed herein addresses this need.

SUMMARY OF THE INVENTION

The present invention is an improved method of measuring a small quantity of a first substance, said substance having a short $T_2$ relaxation time, in the presence of a second substance, said second substance having a long $T_2$ relaxation time. In a static magnetic field, a first excitation RF pulse is applied to the mixture of substances. An inversion pulse is applied to refocus the nuclear magnetization of the long relaxation substance. At the moment of maximum spin echo of the long relaxation substance, a second excitation pulse is applied. At the moment immediately after the application of the second excitation pulse, the longitudinal component of the long relaxation substance is inverted from its equilibrium, while the longitudinal component of the short relaxation substance is substantially zero.

By observing the longitudinal component of the long relaxation substance alone, it is possible to obtain a time after being inverted by the second excitation pulse value at which said longitudinal component of said long relaxation substance will cross zero. At the moment of zero crossing, a third excitation pulses is applied followed by a sequence of inversion pulses. The combination of said third excitation pulses and the sequence of inversion pulses comprise a CPMG pulse sequence. If it is not possible to determine zero crossing by the method stated above, it can be noted that applying the CPMG sequence produces a set of transverse spin echoes for non-zero longitudinal components of the long relaxation substance. Zero crossing can thus be determined by minimization of said spin echoes. When said third excitation pulse is applied at the moment of said zero crossing, the signal of the long relaxation substance is minimized and the relaxation signal of the short relaxation substance can then be observed.

BRIEF DESCRIPTION OF THE DRAWINGS

The present invention is best understood by reference to the; accompanying figures in which.

DESCRIPTION OF THE PREFERRED EMBODIMENT

Figure 1:
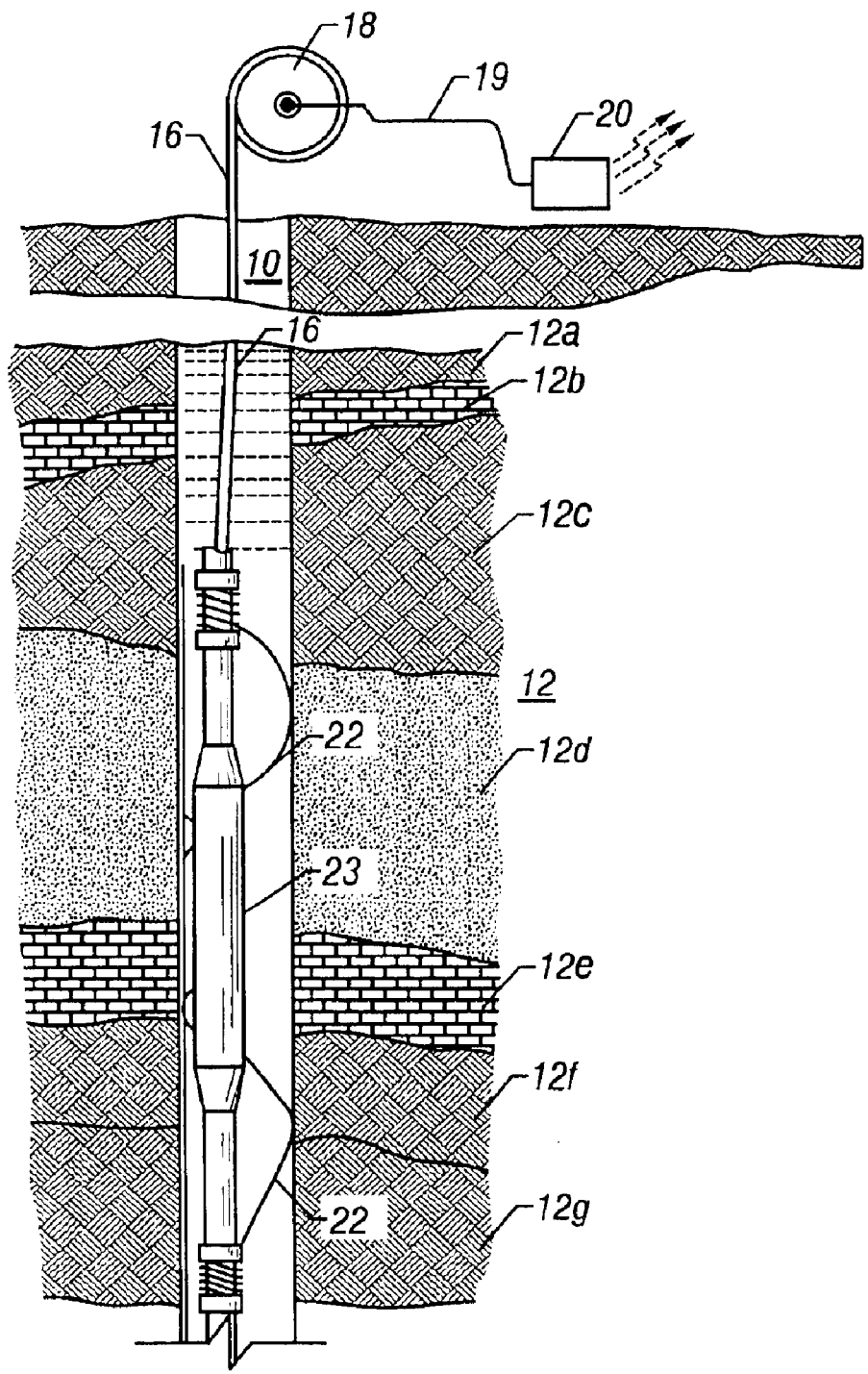
FIG. 1 (Prior Art) depicts a typical NMR logging tool conveyed within a borehole.

FIG. 1 depicts a borehole 10 which has been drilled in a typical fashion into a subsurface geological formation 12 to be investigated for potential hydrocarbon-producing reservoirs. An NMR logging tool 14 has been lowered into the hole 10 by means of a cable 16 and appropriate surface equipment represented diagrammatically by a reel 18 and is being raised through the formation 12 comprising a plurality of layers 12a through 12g of differing composition, to log one or more of the formation's characteristics. The NMR logging tool 23 is provided with bowsprings 22 to maintain the tool in an eccentric position within the borehole with one side of the tool in proximity to the borehole wall. Signals generated by the tool 23 are passed to the surface through the cable 16 and from the cable 16 through another line 19 to appropriate surface equipment 20 for processing, recording and/or display or for transmission to a another site for processing, recording and/or display. It is to be noted that processing may also be done, in part or in whole, by a downhole processor.

Figure 1A:
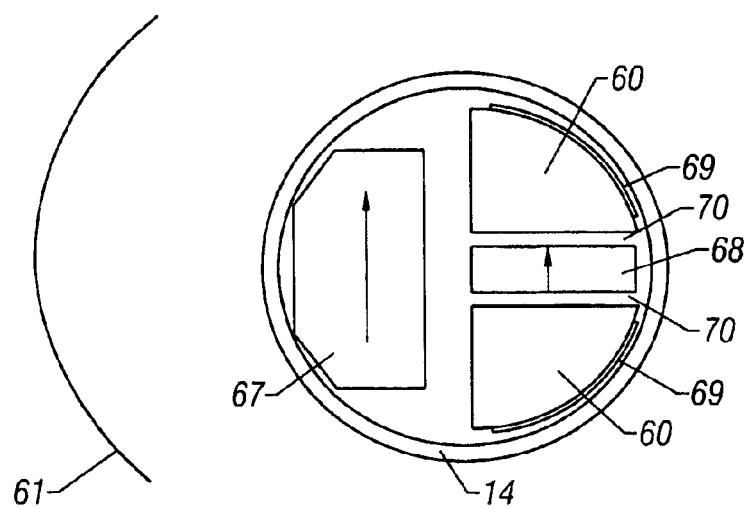
FIG. 1A (prior art) shows the magnet and antenna configuration of a preferred device for the method of the present invention.

FIG. 1A schematically illustrates a preferred embodiment of the present invention for the structure of the NMR tool. This is described fully in U.S. Pat. No. 6,348,792 to Beard et al, having the same assignee as the present invention and the contents of which are fully incorporated herein by reference. It is to be noted that the method of the present invention would be equally effective with other prior art devices used for NMR measurements in boreholes. The tool cross-sectional view in FIG. 1A illustrates a main magnet 67, a second magnet 68, and a transceiver antenna, comprising wires 69 and core material 60. The arrows 71 and 73 depict the polarization (e.g., form the South pole to the North pole) of the main magnet 67 and the secondary magnet (8. A noteworthy feature of the arrangement shown in FIG. 1A is that the polarization of the magnets providing the static field is towards the side of the tool, rather than towards the front of the tool (the right side of FIG. 1A.) as in prior art devices. The importance of this rotated configuration is discussed below.

The second magnet 68 is positioned to augment the shape of the static magnetic field by adding a second magnetic dipole in close proximity to the RF dipole defined by the wires 69 and the soft magnetic core 60. This moves the center of the effective static dipole closer to the RF dipole, thereby increasing the azimuthal extent of the region of examination, the desirability of which has been discussed above. The second magnet 68 also reduces the shunting effect of the high permeability magnetic core 60 on the main magnet 67: in the absence of the second magnet, the DC field would be effectively shorted by the core 60. Thus, the second magnet, besides acting as a shaping magnet for shaping the static field to the front of the tool (the side of the main magnet) also acts as a bucking magnet with respect to the static field in the core 60. Those versed in the art would recognize that the bucking function and a limited shaping could be accomplished simply by having a gap in the core; however, since some kind of field shaping is required on the front side of the tool, in a preferred embodiment of the invention, the second magnet serves both for field shaping and for bucking. If the static field in the core 60 is close to zero, then the magnetostrictive ringing from the core is substantially eliminated.

Figure 2A:
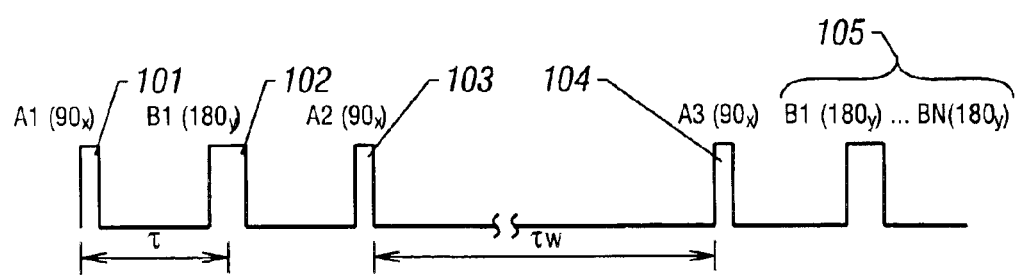
FIG. 2A shows the pulse sequence employed in the present invention.

A novel RF pulse sequence for performing NMR relaxation measurements is presented in FIG. 2A. The sequence is written as $$A1\text{-}\tau\text{-}B1\text{-}\tau\text{-}A2\text{-}TW\text{-}A3\text{-}B2_i \tag{1}$$

The sequence comprises a first excitation pulse A1 (101), a first refocusing pulse B1 (102) delayed by a time τ from the first excitation pulse A1 (101), a forced inversion pulse A2 (103) delayed by the time τ from the first refocusing pulse B1 (102), and a second excitation pulse A3 (104) delayed by the time TW from the forced inversion pulse A2 (103). The sequence also comprises a plurality of refocusing pulses $B2_i$ (105) subsequent to the second excitation pulse A3 (104). The second excitation pulse A3 (104) and the plurality of refocusing pulses $B2_i$ (5) together form a CPMG pulse sequence. The length of time TW depends on the time constant of the longitudinal relaxation of the spins of protons contained in a substance having a long transverse relaxation time. The excitation pulses A1 (101) and A3 (104) and the forced inversion pulse A2 (103) are 90° pulses which tip the nuclear magnetization vector generally through an angle of 90°. The refocusing pulses B1 (102) and $B2_i$ (105) are 180° pulses, which tip the nuclear magnetization vector generally through an angle of 180°. However, the B pulses could also have a reduced tipping angle (less than 180°) as discussed in U.S. Pat. No. 6,163,153 to Reiderman et al.

Figure 2B:
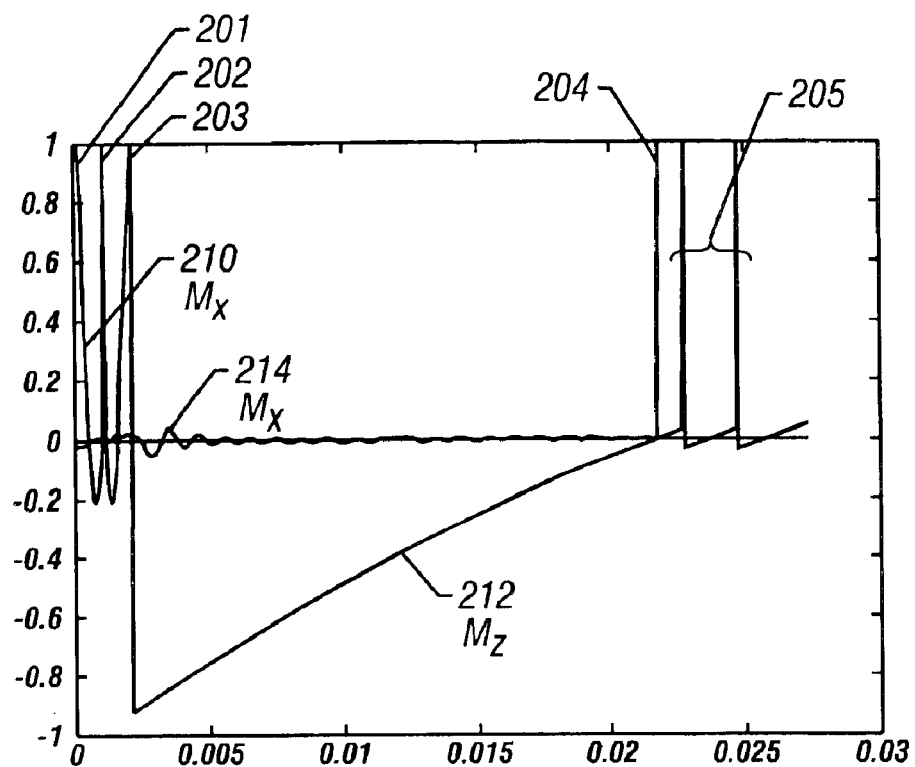
FIG. 2B shows the evolution of nuclear magnetization components for a long $T_1$ and $T_2$ relaxation substance to the pulse sequence of FIG. 1.

FIG. 2b is an example of a computer simulation showing how the transversal and longitudinal nuclear magnetization components evolve for a substance with long relaxation times during application of the pulse sequence presented in Equation 1. To illustrate the invention, a long relaxation substance is stated as having To $T_1=T_2'=30$ msec where $T_2'$ indicates a substance having a long relaxation time. A static magnetic field oriented in the +z-direction is originally applied to the substance, thereby aligning the individual nuclear magnetization vectors along the +z axis. The magnetization vector of the substance, comprising the individual nuclear magnetization vectors, is originally in an equilibrium state and is oriented in the +z direction. The first excitation pulse A1 (201) rotates the nuclear magnetization vector from its equilibrium state (parallel to Z-axis) by 90° and into an X-Y plane having the z-axis as its normal. The subsequent magnetization vector component, stated as $M_x$ (210) without loss of generality, then de-phases (corresponding to a FID) due mainly to the inhomogeneity of the static magnetic field. First refocusing pulse B1 (202) rotates the dephased vectors by 180° enabling a spin echo to occur at the time 2τ. Due to the long $T_1$ times, the longitudinal component $M_z$ (210) experiences insignificant growth and is substantially zero at time t=2τ. Refocused at time t=2τ, the transversal magnetization $M_x$ (210) is then roe 90° by the forced inversion pulse A2 (203) to lie in the direction opposite to the equilibrium, in the -z-direction. After the application of pulse A2 (203), the longitudinal magnetization $M_z$ (212) begins to evolve from its inverted state back to the equilibrium state. On its approach towards equilibrium, $M_z$ (212) crosses through a point of zero net magnetization, herein referred to as the zero axis. At the moment of generally crossing zero, the second excitation pulse A3 (204) is applied. The longitudinal component $M_x$ prior to application of pulse A2 (203) is tilted into the X-Y plane and becomes the transverse component $M_x$ (214). This transverse component K (214) is insignificant and diminishing for the time TW between pulse A2 (203) and pulse A3 (204). For this example, the applied pulse (204) results in an absence of any transverse component of the magnetization and, correspondingly, no signal induced in the NMR antenna during the application of the plurality of refocusing pulses $B2_i$ (205).

Figure 3:
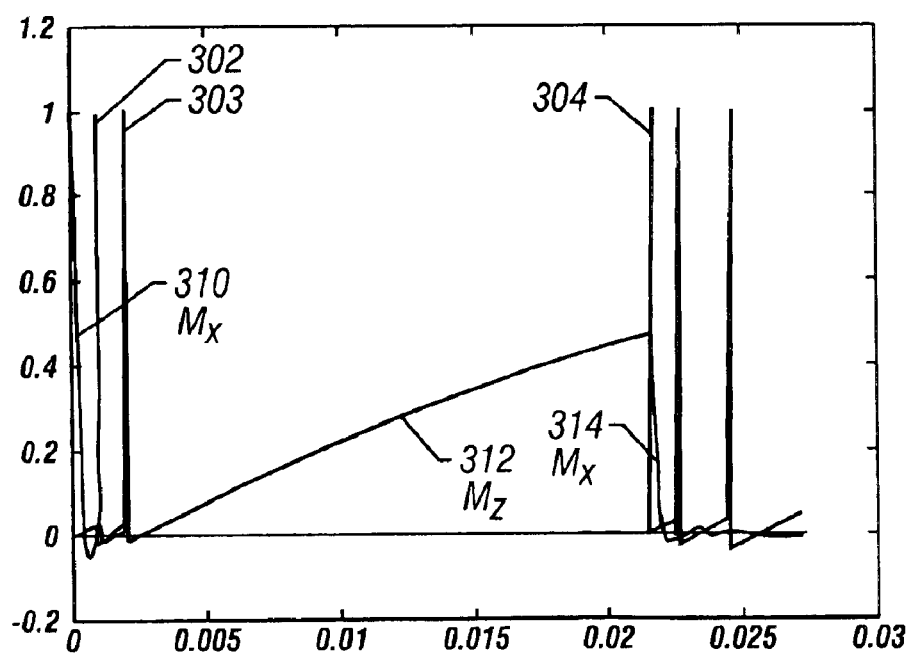
FIG. 3 shows the evolution of nuclear magnetization components for a short $T_2$ relaxation substance to the pulse sequence of FIG. 1.

An essentially different situation takes place in the case of a substance having a short transverse relaxation rate, indicated as $T_2$ with $T_1 \gg T_2$, as is presented in FIG. 3. By setting τ according to the inequality $T_2 \ll \tau \ll T_1$ we ensure that no spin echo from the short $T_2$ relaxation substance is created. At the moment immediately prior to application of the B1 pulse (302) the transverse component has significantly dephased to zero. As a consequence, pulse B1 does nor produce a spin echo at time t=2τ and immediately prior to the first inversion pulse (303), the transverse component is substantially zero. Thus, after application of the first inversion pulse (303), the longitudinal component of the magnetization $M_x$ (312) is generally zero. This zero value is in contrast to the substantial inverted component of the long relaxation substance shown in FIG. 2b. After the elapsed time TW and immediately prior to the application of the second excitation pulse (304), the magnetization vector $M_z$ (312) has practically reached its equilibrium. Again, this is in contrast to the situation with the long $T_2'$ relaxation substance of FIG. 2b, wherein the longitudinal magnetization vector $M_z$ (212) is generally zero at the moment of application of the pulse A3 (204). The pulse (304) hence tips the $M_z$ (312) magnetization into the X-Y plane to generate a FID signal (314) in the NMR receiving antenna.

Figure 4A:
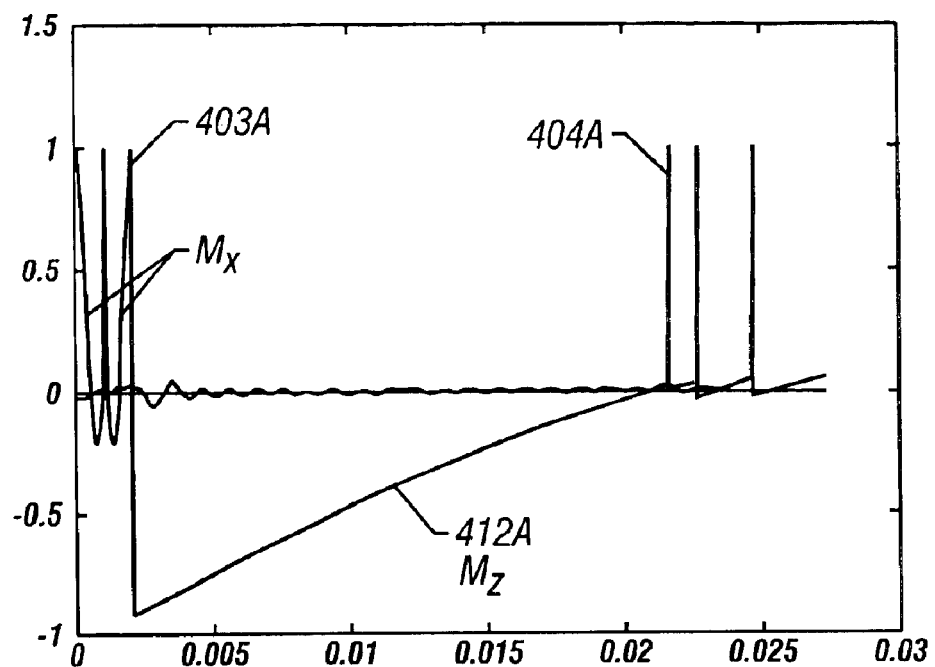
FIG. 4A shows a computer simulation of the evolution of nuclear magnetization components in a mixture of short $T_2$ and long $T_2'$ relaxation substances.
Figure 4B:
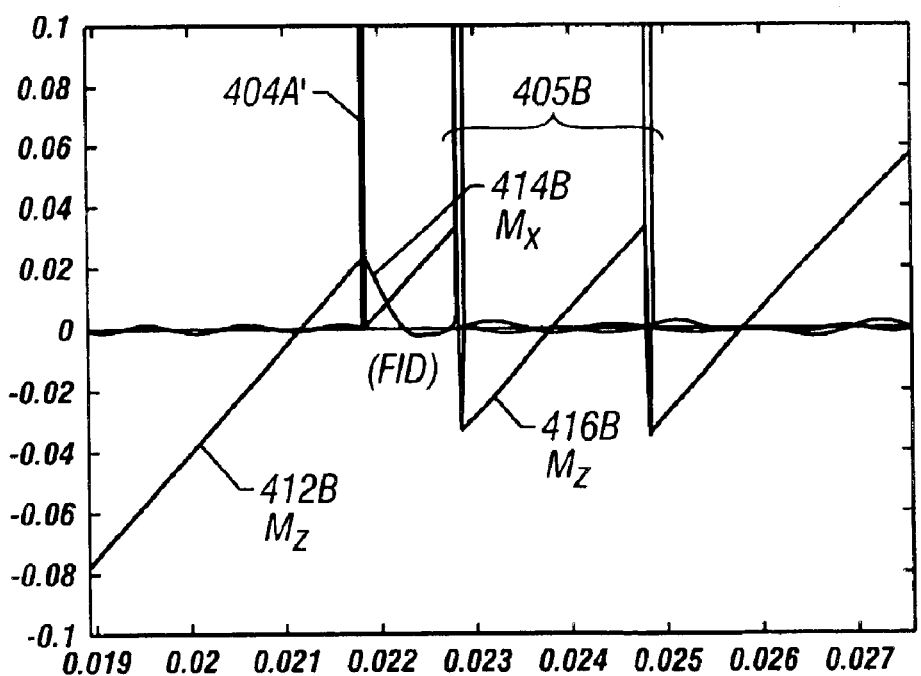
FIG. 4B shows an expanded view of FIG. 4A.

FIGS. 4A, 4B present the result of computer modeling for a mixture of two substances having different relaxation rates and reacting to the influence of the pulse sequence of Equation 1. The slow relaxation substance has relaxation times $T_1=T_2'=30$ msec. The fast relaxation substance, in quantity of 5% of the long relaxation substance, has relaxation parameters $T_1=30$ msec, $T_2=0.5$ msec. It is clear that for a mixture of long relaxation signals there will be a point after the application of the inversion pulse (403A) at which the longitudinal component of magnetization (412A) crosses the zero axis. FIG. 4B presents an enlarged section of FIG. 4A in the vicinity of the second excitation pulse A3 (404A), with pulse 404A of FIG. 4B representing pulse 404A of FIG. 4A. At the moment of zero crossing, the relatively small signal of a short relaxation FID signal (414B) can be measured. The longitudinal component $M_z$ (416B) experiences growth toward equilibrium as well as 180° inversions due to the pulse sequence $B2_i$ (405B).

The moment of application of pulse A3 (404A) is determined by observing the point at which the longitudinal component $M_z$ (412B) only for the long relaxation substance crosses the zero axis. In case the zero-crossing point can not be determined in advance by using measurement results on the long relaxation substances only, or if the moment of crossing the zero axis varies due to temperature dependence of $T_1$ relaxation time for the long relaxation substances, then the procedure described below can be preferably used to find the zero crossing point. The CPMG sequence, comprising pulse (404B) and the plurality of pulses (405B), generates a train of spin echoes. If the delay after pulses in the plurality of pulses (405B) exceeds the $T_2$ relaxation time for the short relaxation substance, then any echoes seen between pulses (405B) represent only those echoes from the long relaxation substances. Thus, by varying the time interval TW between the pulses A2 (403A) and A3 (404A) in FIG. 4A, it is possible to zero out the echo amplitudes $M_x$ (414B) and thus to use the zeroing of echo amplitudes as an indicator. This method enables an operator to obtain a high precision elimination of the signal from the slowly relaxing substance. FIG. 4B is an illustration for the situation of substantially zero echo amplitudes and, correspondingly, for the fact that the FID signal (414B) after the pulse (404B) represents the contributions significantly from the short relaxation substance.

Figure 4C:
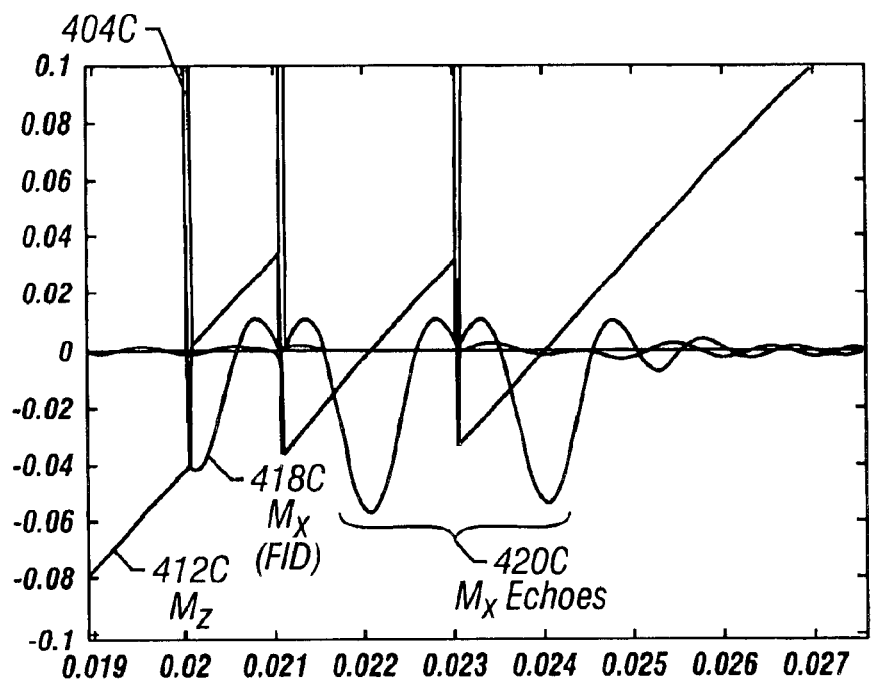
FIG. 4C shows an expanded view of FIG. 4A with reduced wait time.
Figure 4D:
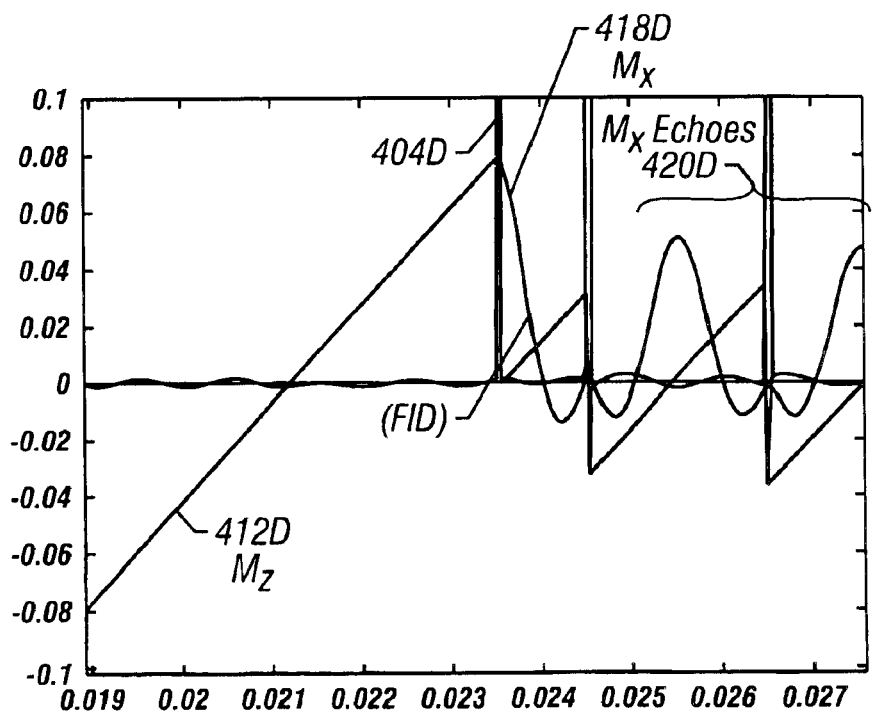
FIG. 4D shows an expanded view of FIG. 4A with expanded wait time.

To further illustrate this technique, FIGS. 4C and 4D represent the situations when TW is 8% smaller and 8% larger, respectively, than its value used in FIG. 4B. Comparison of FIGS. 4C and 4D illustrates the high sensitivity of the echo signal $M_x$ to relatively small departures of TW from its optimum value. In FIG. 4C, the $M_z$ component (412C) is has a net negative value at the moment of application of the second excitation pulse (404C). The resultant $M_x$ component (418C) subsequent leads to $M_x$ echoes (420C) having substantially negative polarity. Similarly, In FIG. 4D, the $M_z$ component (412D) has a net position value at the moment of application of the second excitation pulse (404D). The resultant $M_x$ component (418D) subsequent leads to $M_z$ echoes (420D) having substantially positive polarity.

In another embodiment of the invention, after the wait time TW needed to zero out the free induction decay (FID) signal $M_x$ (414B) is determined, the TW is altered slightly. This is followed by a single A3 pulse. Analysis of the free induction decay signal can then be used for determining the relative quantities of the fast and slowly relaxing components.

Figure 5A:
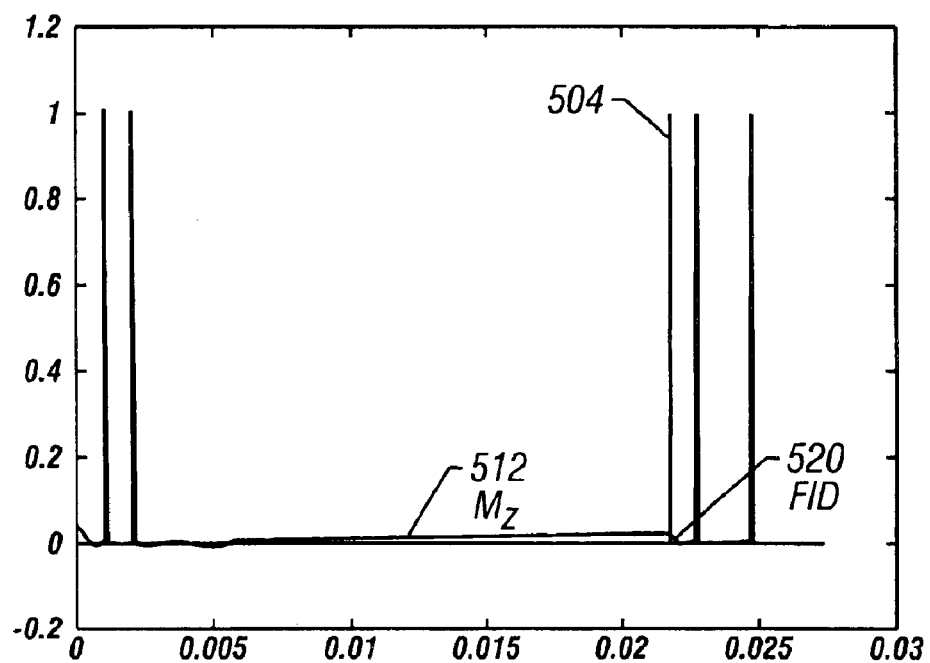
FIG. 5A shows the result of modeling corresponding to a short $T_2$ relaxation substance.
Figure 5B:
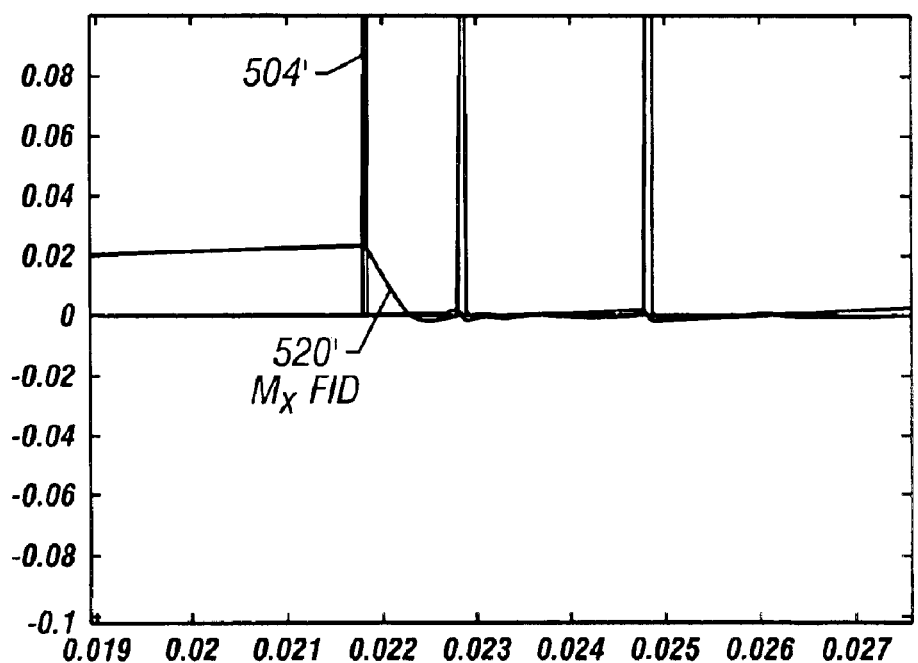
FIG. 5B shows an expanded view of FIG. 5A.

FIGS. 5A and 5B shows the result of modeling corresponding to the 5% quantity of short $T_2$ relaxation substance only affected by the pulse sequence of Equation 1. FIG. 5A shows the growth of the longitudinal component $M_z$ (512) and the FID (520) that results from applied pulse 504. FIG. 5B is an enlargement of FIG. 5A in the vicinity of pulse 504, relabeled as 504' in FIG. 5B. Comparison of the short relaxation FID (520') signal after the second excitation pulse (504') in FIG. 5B with the recovered FID signal 414 in FIG. 4B shows that the signal from a large amount of the long relaxation substance in the mixture is substantially eliminated from FIG. 4B. Thus, the proposed technique enables measuring a very small amount of the short relaxation substance mixed with a large amount of long relaxation substances.

The present invention has been described with reference to a wireline device. However, the principles of the invention may also be embodied in and used with MWD devices conveyed on a drilling tubular such as a drillstring or coiled tubing.

While the foregoing disclosure is directed to the preferred embodiments of the invention, various modifications will be apparent to those skilled in the art. It is intended that all variations within the scope and spirit of the appended claims be embraced by the foregoing disclosure.

What is claimed is:

1. A method of identifying a presence of a first fluid having a first transverse nuclear magnetic spin relaxation time $T_1$ in a mixture of earth formation fluids with a second fluid having a second transverse nuclear magnetic spin relaxation time $T_2'$ greater than said first transverse relaxation time, the method comprising:
   (a) producing a static magnetic field in said mixture of said earth formation fluids;
   (b) applying a pulse sequence having pulses

A1-τ-B1-τ-A2-TW-A3 to said mixture where A1 is a first excitation pulse, τ is a Carr-Purcell time, B1 is a first refocusing pulse, A2 is forced inversion pulse, A3 is a second excitation pulse, and TW is a wait time wherein a resulting signal from said second fluid in said earth formation is substantially zero and
   (c) determining said presence by analyzing signals after said second excitation pulse.

2. The method of claim 1 wherein said first excitation pulse comprises a pulse having a tip angle substantially equal to 90°.

3. The method of claim 1 wherein said second excitation pulse comprises a pulse having a tip angle substantially equal to 90°.

4. The method of claim 1 wherein said first refocusing pulse comprises a pulse having a tip angle substantially equal to 180°.

5. The method of claim 1 further comprising determining said value of TW by applying a sequence of refocusing pulses $B_{2i}$ after said second excitation pulse and determining a value of TW for which substantially no spin echo signals are produced by said sequence of refocusing pulses.

6. The method of claim 5 wherein at least one of said sequence of refocusing pulses comprises a pulse with a tip angle substantially equal to 180°.

7. The method of claim 1 further selecting τ to satisfy the condition $$T_2' \gg \tau \gg T_2.$$

8. The method of claim 5 further comprising:
   (i) repeating (b) with different values of TW until no free induction decay signal after the second excitation pulse A3 is produced;
   (ii) repeating (b) with a value of TW altered from the value determined in (i); and
   (iii) analyzing a resulting free induction decay signal.

9. The method of claim 1 further comprising conveying a magnet on a logging tool into a borehole into said earth formation.

10. The method of claim 9 wherein said logging tool is conveyed on a wireline.

11. The method of claim 9 wherein said logging tool is conveyed on a drilling tubular.

12. A system for identifying a presence of first fluid having a first transverse nuclear spin relaxation time $T_2$ in a mixture of fluids in an earth formation with a second fluid having a second transverse spin relaxation time $T_2'$ greater than said first transverse relaxation time, the system comprising:
   (a) a logging tool conveyed into a borehole into said earth formation,
   (b) a magnet on said logging tool which produces a static field in a region of said earth formation including said mixture;
   (b) a transmitter on said logging tool which applies a radio frequency pulse sequence

A1-τ-B1-τ-A2-TW-A3 to said mixture in said region, where A1 is a first excitation pulse, τ is a Carr-Purcell time, B1 is a first refocusing pulse, A2 is forced inversion pulse, and A3 is a second excitation pulse,
   (c) a receiver on said logging tool which receives signals resulting from said nuclear spins resulting from application of said pulse sequence;
   (d) a processor which:
      (A) determines a value of TW for which a resulting signal from said second fluid is substantially zero, and
      (B) identifies said presence of said first fluid by analyzing signals after said second excitation pulse.

13. The system of claim 12 wherein said first excitation pulse comprises a pulse having a tip angle substantially equal to 90°.

14. The system of claim 12 wherein said second excitation pulse comprises a pulse having a tip angle substantially equal to 90°.

15. The system of claim 12 wherein said processor determines said value of TW by further applying a sequence of refocusing pulses $B_{21}$ after said second excitation pulse and determining a value of TW for which substantially no spin echo signals are produced by said sequence of refocusing pules.

16. The system of claim 12 wherein said first refocusing pulse comprises a pulse having a tip angle substantially equal to 180°.

17. The system of claim 15 wherein at least one of said sequence of refocusing pulses comprises a pulse with a tip angle substantially equal to 180°.

18. The system of claim 12 wherein $T_2'>>\tau>>T_2$.

19. The system of claim 12 wherein said processor further performs:

(i) a repetition of (b) in claim 13 with different values of TW until no free induction decay signal after the second excitation pulse A3 is produced;

(ii) a repetition of (b) in claim 13 with the value of TW altered from the value determined in (i); and (iii) analyzes a resulting free induction decay signal.

20. The system of claim 12 further comprising a wireline for conveying said logging tool into said borehole.

21. The system of claim 12 further comprising a drilling tubular for conveying said logging tool into said borehole.

22. The system of claim 12 wherein said processor is on said logging tool.

* * * * *